United States Patent
Seitz et al.

Patent Number: 5,482,972
Date of Patent: Jan. 9, 1996

[54] SUBSTITUTED AMINO ACID AMIDES

[75] Inventors: Thomas Seitz; Heinz-Wilhelm Dehne, both of Monheim, Germany

[73] Assignee: Bayer Aktiengesellschaft, Leverkusen, Germany

[21] Appl. No.: 234,437

[22] Filed: Apr. 28, 1994

Related U.S. Application Data

[63] Continuation of Ser. No. 8,280, Jan. 25, 1993, abandoned.

[30] Foreign Application Priority Data

Feb. 4, 1992 [DE] Germany ............... 42 03 084.6

[51] Int. Cl.⁶ ..................... A61K 31/27; C07C 333/04
[52] U.S. Cl. ............................. 514/487; 558/240
[58] Field of Search ..................... 558/240; 514/487

[56] References Cited

U.S. PATENT DOCUMENTS

| | | | |
|---|---|---|---|
| 4,138,485 | 2/1979 | Nakamizo et al. | 424/248.5 |
| 4,559,083 | 12/1985 | Balogh et al. | 71/100 |
| 4,944,796 | 7/1990 | Wee | 71/118 |
| 5,210,084 | 5/1993 | Wollweber et al. | 514/237.5 |
| 5,331,006 | 7/1994 | Horwell et al. | 514/487 X |

FOREIGN PATENT DOCUMENTS

| | | |
|---|---|---|
| 0398072 | 11/1990 | European Pat. Off. |
| 655305 | 4/1986 | Switzerland. |

OTHER PUBLICATIONS

Chemical & Pharmaceutical Bulletin, vol. 19, No. 5, May 1971; "Studies on Optically Active Amino Acids . . . ", K. Ishikawa et al; cover page and pp. 912–929.

*Primary Examiner*—Johann Richter
*Assistant Examiner*—Michael G. Ambrose
*Attorney, Agent, or Firm*—Sprung Horn Kramer & Woods

[57] ABSTRACT

There are described new amino acid amides of the formula (I)

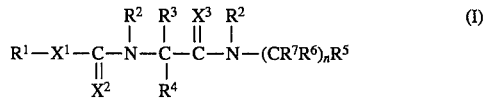

in which
n, $R^1$, $R^2$, $R^4$, $R^5$, $R^6$, $R^7$, $X^1$, $X^2$ and $X^3$ having the meaning given in the description, and a process for their preparation.

The new amino acid amides of the formula (I) are used as pesticides,

15 Claims, No Drawings

SUBSTITUTED AMINO ACID AMIDES

This is continuation of application Ser. No. 08/008,280, filed Jan. 25, 1992, now abandoned.

The invention relates to new substituted amino acid amides, to a process for their preparation, and to their use as pesticides.

It is known that certain substituted amino acid amides such as, for example, the compound $N^{\alpha}$-(t-butyloxycarbonyl)-L-valine-[N-(1-phenylethyl)-amide] or the compound $N^{\alpha}$-(t-butyloxycarbonyl)-L-valine-{N-[1-(2-chlorophenyl)ethyl]-amide} or the compound $N^{\alpha}$-(t-butyloxycarbonyl)-L-valine-{N-methyl-N-[1-(4-chlorophenyl)-ethyl -amide}, have fungicidal properties (cf., for example, EP 398,072).

However, the activity of these previously known compounds is not entirely satisfactory in all fields of application, in particular when low amounts and concentrations are applied.

New substituted amino acid amides of the general formula

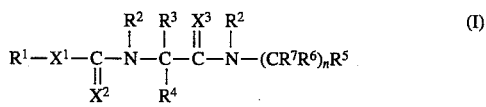

in which
R$^1$ represents alkyl, alkenyl, alkinyl, halogenoalkyl, halogenoalkenyl, halogenoalkinyl, cycloalkyl, cycloalkenyl, or in each case optionally substituted arylalkyl, aryl, heteroarylalkyl or heteroaryl,
R$^2$ represents hydrogen, alkyl or cycloalkyl,
R$^3$ represents hydrogen, alkyl or cycloalkyl and
R$^4$ represents alkyl, cycloalkyl, or
R$^3$ and R$^4$ together with the carbon atom to which they are bonded represent a cycloalkyl ring,
R$^5$ represents in each case optionally substituted cycloalkyl, cycloalkenyl, aryl, heterocyclyl, cycloalkylalkyl, cycloalkenyl, arylalkyl or heterocyclylalkyl,
R$^6$, R$^7$ independent from each other represent hydrogen or in each optionally substituted alkyl, alkenyl, alkinyl, cycloalkyl, cycloalkenyl, aryl, hetero-cyclyl, cycloalkylalkyl, cycloalkenylalkyl, arylalkyl, heterocyclylalkyl, or together form a cycloalkylring,
X$^1$ represents oxygen or sulphur,
X$^2$ represents oxygen or sulphur, and
X$^3$ represents oxygen or sulphur,
n represents 0, 1, 2 or 3
but where at least one of the substituents X$^1$, X$^2$ and/or X$^3$ represents sulphur.

If appropriate, the compounds of the formula (I) can exist in the form of geometric and/or optical isomers or isomer mixtures of various compositions, depending on the nature of the substituents. The invention claims the pure isomers as well as the isomer mixtures.

Furthermore, it has been found that the new substituted amino acid amides of the general formula (I)

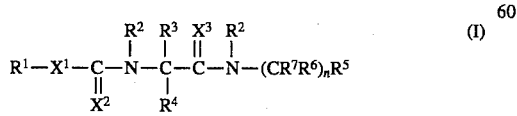

in which
n, R$^1$, R$^2$, R$^4$, R$^5$, R$^6$, R$^7$, X$^1$, X$^2$, and X$^3$ have the above mentioned meaning, are obtained when substituted amino acids of the formula (II)

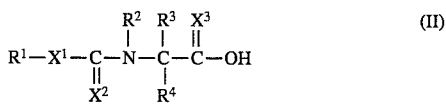

in which
R$^1$, R$^2$, R$^3$, R$^4$ X$^1$, and X$^3$ have the abovementioned meaning,
are reacted with amines of the formula (III)

$$R^2HN-(CR^7R^6)_nR^5 \qquad (III)$$

in which
n, R$^2$, R$^5$, R$^6$ and R$^7$ have the above mentioned meaning,
if appropriate in the presence of a diluent and if appropriate in the presence of a reaction auxiliary.

Finally, it has been found that the new substituted amino acid amides of the general formula (I) have a good activity against pests.

Surprisingly, the substituted amino acid amides of the general formula (I) according to the invention show a considerably better fungicidal activity than the substituted amino acid amides known from the prior art such as, for example, the compound $N^{\alpha}$-(t-butyloxycarbonyl)-L-valine-[N-(1-phenylethyl)-amide] or the compound $N^{\alpha}$-(t-butyloxycarbonyl)-L-valine-{N-[1-(2 -valine-{N-[1-(2-chlorophenyl)ethyl]-amide or the compound $N^{\alpha}$-(t-butyloxycarbonyl)-L-valine-{N-methyl-N-[1-(4-chlorophenyl)ethyl]-amide},
which are similar compounds chemically and from the point of view of their action.

Formula (I) provides a general definition of the substituted amino acid amides according to the invention. Preferred compounds of the formula (I) are those in which R$^1$ represents in each case straight-chain or branched alkyl having 1 to 8 carbon atoms, alkenyl having 2 to 8 carbon atoms, alkinyl having 2 to 8 carbon atoms, halogenoalkyl having 1 to 6 carbon atoms and 1 to 13 identical or different halogen atoms, halogenoalkenyl having 2 to 6 carbon atoms and 1 to 11 identical or different halogen atoms, halogenoalkinyl having 2 to 6 carbon atoms and 1 to 11 identical or different halogen atoms, cycloalkyl having 3 to 8 carbon atoms, cycloalkenyl having 3 to 8 carbon atoms, or represents arylalkyl, aryl, heteroarylalkyl or heteroaryl, each of which has, if appropriate, 6 to 10 carbon atoms in the aryl moiety, or 2 to 9 carbon atoms and 1 to 4 identical or different hetero atoms—in particular nitrogen, oxygen and/or sulphur—in the heteroaryl moiety and, if appropriate, 1 to 6 carbon atoms in the straight-chain or branched alkyl moiety, and each of which is optionally monosubstituted or polysubstituted in the aryl moiety, or heteroaryl moiety, by identical or different substituents, suitable aryl or heteroaryl substituents in each case being:
halogen, cyano, nitro, hydroxyl, formyl, hydroxycarbonyl, aminocarbonyl, aminosulphonyl, in each case straight-chain or branched alkyl, alkoxy, alkoxyalkyl, alkylthio, alkylsulphinyl, alkylsulphonyl, alkoxysulphonyl, alkylsulphonyloxy or dialkylamino, each of which has 1 to 4 carbon atoms in the individual alkyl moieties, in each case straight-chain or branched halogenoalkyl, halogenoalkoxy, halogenoalkylthio, halogenoalkylsulphinyl or halogenoalkylsulphonyl, each of which has 1 to 4 carbon atoms and 1 to 9 identical or different halogen atoms, in each case straight-chain or branched alkylcarbonyl, alkylcarbonyloxy, alkoxycarbonyl, N-alkylaminocarbonyl, N,N-dialkylaminocarbonyl, alkylcarbonylamino, alkylcarbonylaminoalkyl or alkoximinoalkyl, each of which has 1 to 4 carbon atoms in the individual alkyl moieties, and phenyl, phenoxy, phenylcarbonyl, phenoxycarbonyl or phenylcarbonyloxy, each of which is optionally monosubstituted or polysubstituted in the phenyl moiety by identical or different substituents from the series comprising halogen and/or straight-chain or branched alkyl having 1 to 4 carbon atoms, $R^2$ represents hydrogen, straight-chain or branched alkyl having 1 to 8 carbon atoms or cycloalkyl having 3 to 8 carbon atoms, $R^3$ represents hydrogen, straight-chain or branched alkyl having 1 to 8 carbon atoms or cycloalkyl having 3 to 8 carbon atoms and $R^4$ represents straight-chain or branched alkyl having 1 to 8 carbon atoms or cycloalkyl having 3 to 8 carbon atoms, or $R^3$ and $R^4$ together with the carbon atom to which they are bonded represent a 3- to 8-membered cycloalkyl ring, $R^5$ represents cycloalkyl, cycloalkylalkyl, cycloalkenylalkyl or cycloalkenyl, each of which has 3 to 8 carbon atoms and each of which is optionally monosubstituted or polysubstituted by identical or different substituents, suitable cycloalkyl or cycloalkenyl substituents in each case being: halogen, hydroxyl, in each case straight-chain or branched alkyl, alkanediyl, alkoxy, alkoxyalkyl, alkylthio or dialkylamino, each of which has 1 to 6 carbon atoms in the individual alkyl moieties, or in each case straight-chain or branched halogenoalkyl, halogenoalkoxy, halogenoalkylthio, each of which has 1 to 4 carbon atoms and 1 to 9 identical or different halogen atoms, moreover aryl or arylalkyl having 6 to 10 carbon atoms or heterocyclyl or heterocyclylalkyl having 2 to 9 carbon atoms and 1 to 4 identical or different hetero atoms—in particular nitrogen, oxygen and/or sulphur—each of these aryl heterocyclyl radicals optionally being monosubstituted or polysubstituted by identical or different substituents, suitable aryl or heterocyclyl substituents in each case being those mentioned in the case of $R^1$, $R^6$, $R^7$ independent from each other represent hydrogen, in each case straight-chain or branched alkyl having 1 to 8 carbon atoms, cyanoalkyl having 2 to 9 carbon atoms, alkenyl having 2 to 8 carbon atoms, alkinyl having 2 to 8 carbon atoms, or cycloalkyl, cycloalkylalkyl, cycloalkenyl or cycloalkenylalkyl, each of which has 3 to 8 carbon atoms in the cycloalkyl or cycloalkenyl moiety and, if appropriate, 1 to 6 carbon atoms in the straight-chain or branched alkyl moiety, and each of which is optionally monosubstituted or polysubstituted in the cycloalkyl or cycloalkenyl moiety by identical or different substituents, suitable cycloalkyl or cycloalkenyl substituents in each case being:

halogen, hydroxyl, in each case straight-chain or branched alkyl, alkanediyl, alkoxy, alkoxyalkyl, alkylthio or dialkylamino, each of which has 1 to 6 carbon atoms in the individual alkyl moieties, or in each case straight-chain or branched halogenoalkyl, halogenoalkoxy, halogenoalkylthio, each of which has 1 to 4 carbon atoms and 1 to 9 identical or different halogen atoms, moreover arylalkyl, aryl, heterocyclylalkyl or heterocyclyl, each of which has, if appropriate, 6 to 10 carbon atoms in the aryl moiety or 2 to 9 carbon atoms and 1 to 4 identical or different hetero atoms—in particular nitrogen, oxygen and/or sulphur—in the heterocyclyl moiety and, where appropriate, 1 to 6 carbon atoms in the straight-chain or branched alkyl moiety, and each of which is optionally monosubstituted or polysubstituted in the aryl or heterocyclyl moiety by identical or different substituents, suitable aryl or heterocyclyl substituents in each case being those mentioned in the case of $R^1$, or together form a cycloalkylring with 1 to 7 carbon atoms, $X^1$ represents oxygen or sulphur, $X^2$ represents oxygen or sulphur and $X^3$ represents oxygen or sulphur, n represents 0, 1, 2 or 3, but where at least one of the substituents $X^1$, $X^2$ and/or $X^3$ represents sulphur.

Particularly preferred compounds of the formula (I) are those in which $R^1$ represents in each case straight-chain or branched alkyl having 1 to 6 carbon atoms, alkenyl having 2 to 6 carbon atoms, alkinyl having 2 to 6 carbon atoms, halogenoalkyl having 1 to 4 carbon atoms and 1 to 9 identical or different halogen atoms, halogenoalkenyl having 2 to 4 carbon atoms and 1 to 7 identical or different halogen atoms, halogenoalkinyl having 2 to 4 carbon atoms and 1 to 7 identical or different halogen atoms, cycloalkyl having 3 to 7 carbon atoms, cycloalkenyl having 3 to 7 carbon atoms, or represents arylalkyl, aryl, heteroarylalkyl or heteroaryl, each of which has, where appropriate, 6 to 10 carbon atoms in the aryl moiety, or 2 to 9 carbon atoms and 1 to 3 identical or different hereto atoms—in particular nitrogen, oxygen and/or sulphur—in the heteroaryl moiety and, where appropriate, 1 to 4 carbon atoms in the straight-chain or branched alkyl moiety, and each of which is optionally monosubstituted to pentasubstituted in the aryl or heteroaryl moiety by identical cal or different substituents, suitable aryl or heteroaryl substituents in each case being:

halogen, cyano, nitro, hydroxyl, formyl, hydroxycarbonyl, aminocarbonyl, aminosulphonyl, in each case straight-chain or branched alkyl, alkoxy, alkoxyalkyl, alkylthio, alkylsulphinyl, alkylsulphonyl, alkoxysulphonyl, alkylsulphonyloxy or dialkylamino, each of which has 1 to 4 carbon atoms in the individual alkyl moieties, in each case straight-chain or branched halogenoalkyl, halogenoalkoxy, halogenoalkylthio, halogenoalkylsulphinyl or halogenoalkylsulphonyl, each of which has 1 to 4 carbon atoms and 1 to 9 identical or different halogen atoms, in each case straight-chain or branched alkylcarbonyl, alkylcarbonyloxy, alkoxycarbonyl, N-alkylaminocarbonyl, N,N-dialkylaminocarbonyl, alkylcarbonylamino, alkylcarbonylaminoalkyl or alkoximinoalkyl, each of which has 1 to 4 carbon atoms in the individual alkyl moieties, and phenyl, phenoxy, phenylcarbonyl, phenoxycarbonyl or phenylcarbonyloxy, each of which is optionally monosubstituted or polysubstituted in the phenyl moiety by identical or different substituents from the series comprising halogen and/or straight-chain or branched alkyl having 1 to 4 carbon atoms, $R^2$ represents hydrogen, straight-chain or branched alkyl having 1 to 6 carbon atoms or cycloalkyl having 3 to 7 carbon atoms, $R^3$ represents hydrogen, straight-chain or branched alkyl having 1 to 6 carbon atoms or cycloalkyl having 3 to 7 carbon atoms and $R^4$ represents straight-chain or branched alkyl having 1 to 6 carbon atoms or cycloalkyl having 3 to 6 carbon atoms, or $R^3$ and $R^4$ together with the carbon atom to which they are bonded represent a 3- to 7-membered cycloalkyl ring, $R^5$ represents cycloalkyl, cycloalkylalkyl, cycloalkenylalkyl or cycloalkenyl, each of which has 3 to 7 carbon atoms and each of which is optionally monosubstituted to pentasubstituted by identical or different substituents, suitable cycloalkyl or cycloalkenyl substituents in each case being: halogen, hydroxyl, in each case straight-chain or branched alkyl, alkanediyl, alkoxy, alkoxyalkyl, alkylthio or dialkylamino, each of which has 1 to 4 carbon atoms in the individual alkyl moieties, or in each case straight-chain or branched halogenoalkyl, halogenoalkoxy, halogenoalkylthio, each of which has 1 to 4 carbon atoms and 1 to 9 identical or different halogen atoms, moreover represents aryl or arylalkyl having 6 to 10 carbon atom,s or heterocyclyl or heterocyclylalkyl having 2 to 9 carbon atoms and 1 to 3 identical or different hereto atoms—in particular nitrogen, oxygen and/or sulphur—each of these aryl or heterocyclyl radicals optionally being monosubstituted to pentasubstituted by identical or different substituents, suitable aryl or heterocyclyl substituents in each case being those mentioned in the case of $R^1$, $R^6$, $R^7$ independent from each other represents hydrogen, in each case straight-chain or branched alkyl having 1 to 6 carbon atoms, cyanoalkyl having 2 to 5 carbon atoms, alkenyl having 1 to 6 carbon atoms, alkinyl having 2 to 6 carbon atoms, or cycloalkyl, cycloalkylalkyl, cycloalkenyl or cycloalkenylalkyl, each of which has 3 to 7 carbon atoms in the cycloalkyl or cycloalkenyl moiety and, where appropriate, 1 to 4 carbon atoms in the straight-chain or branched alkyl moiety, and each of which is optionally monosubstituted to pentasubstituted in the cycloalkyl or , cycloalkenyl moiety by identical or different substituents, suitable cycloalkyl or cycloalkenyl substituents in each case being: halogen, hydroxyl, in each case straight-chain or branched alkyl, alkanediyl, alkoxy, alkoxyalkyl, alkylthio or dialkylamino, each of which has 1 to 4 carbon atoms in the individual alkyl moieties, or in each case straight-chain or branched halogenoalkyl, halogenoalkoxy, halogenoalkylthio, each of which has 1 to 4 carbon atoms and 1 to 9 identical or different halogen atoms, moreover represents arylalkyl, aryl, heterocyclylalkyl or heterocyclyl, each of which has, if appropriate, 6 to 10 carbon atoms in the aryl moiety or 2 to 9 carbon atoms and 1 to 3 identical or different hereto atoms—in particular nitrogen, oxygen and/or sulphur—in the heterocyclyl moiety and, where appropriate, 1 to 4 carbon atoms in the straight-chain or branched alkyl moiety, and each of which is optionally monosubstituted to pentasubstituted in the aryl or heterocyclyl moiety by identical or different substituents, suitable aryl or heterocyclyl substituents in each case being those mentioned in the case of $R^1$, or together form a cycloalkylring with 3 to 6 carbon atoms, n represents 0, 1, 2 or 3, $X^1$ represents oxygen or sulphur, $X^2$ represents oxygen or sulphur and $X^3$ represents oxygen or sulphur, but where at least one of the substituents $X^1$, $X^2$ and/or $X^3$ represents sulphur.

Very particularly preferred compounds of the formula (I) are those in which $R^1$ represents in each case straight-chain or branched alkyl having 2 to 5 carbon atoms, alkenyl having 2 to 4 carbon atoms, alkinyl having 2 to 4 carbon atoms, halogenoalkyl having 1 or 2 carbon atoms and 1 to 5 identical or different halogen atoms, halogenoalkenyl having 2 to 3 carbon atoms and 1 to 5 identical or different halogen atoms, halogenoalkinyl having 2 to 3 carbon atoms and 1 to 5 identical or different halogen atoms, cycloalkyl having 3 to 6 carbon atoms, cycloalkenyl having 3 to 6 carbon atoms, or represents phenylalkyl or phenyl, each of which has, where appropriate, 1 to 4 carbon atoms in the straight-chain or branched alkyl moiety, and each of which is optionally monosubstituted to trisubstituted in the phenyl moiety by identical or different substituents, suitable phenyl substituents in each case being:

halogen, cyano, nitro, hydroxyl, formyl, hydroxycarbonyl, aminocarbonyl, aminosulphonyl, in each case straight-chain or branched alkyl, alkoxy, alkoxyalkyl, alkylthio, alkylsulphinyl, alkylsulphonyl, alkoxysulphonyl, alkylsulphonyloxy or dialkylamino, each of which has 1 to 3 carbon atoms in the individual alkyl moieties, in each case straight-chain or branched halogenoalkyl, halogenoalkoxy, halogenoalkylthio, halogenoalkylsulphinyl or halogenoalkylsulphonyl, each of which has 1 or 2 carbon atoms and 1 to 5 identical or different halogen atoms, in each case straight-chain or branched alkylcarbonyl, alkylcarbonyloxy, alkoxycarbonyl, N-alkylaminocarbonyl, N,N-dialkylaminocarbonyl, alkylcarbonylamino, alkylcarbonylaminoalkyl or alkoximinoalkyl, each of which has 1 to 3 carbon atoms in the individual alkyl moieties, and phenyl, phenoxy, phenylcarbonyl, phenoxycarbonyl or phenylcarbonyloxy, each of which is optionally monosubstituted or polysubstituted in the phenyl moiety by identical or different substituents from the series comprising halogen and/or straight-chain or branched alkyl having 1 to 3 carbon atoms, $R^2$ represents hydrogen, straight-chain or branched alkyl having 1 to 4 carbon atoms or cycloalkyl having 3 to 6 carbon atoms, $R^3$ represents hydrogen, straight-chain or branchedalkyl having 1 to 4 carbon atoms or cycloalkyl having 3 to 6 carbon atoms and $R^4$ represents straight-chain or branched alkyl having 1 to 4 carbon atoms or cycloalkyl having 3 to 6 carbon atoms, or $R^3$ and $R^4$ together with the carbon atom to which they are bonded represent a 3- to 6-membered cycloalkyl ring, $R^5$ represents cycloalkyl, cycloalkylalkyl, cycloalkenylalkyl or cycloalkenyl, each of which has 3 to 6 carbon atoms and each of which is optionally monosubstituted to trisubstituted by identical or different substituents, suitable cycloalkyl or cycloalkenyl substituents in each case being:

halogen, hydroxyl, in each case straight-chain or branched alkyl, alkanediyl, alkoxy, alkoxyalkyl, alkylthio or dialkylamino, each of which has 1 to 3 carbon atoms in the individual alkyl moieties, or in each case straight-chain or branched halogenoalkyl, halogenoalkoxy, halegenoalkylthio, each of which has 1 or 2 carbon atoms and 1 to 5 identical or different halogen atoms, moreover represents phenyl or phenylalkyl or heterocyclyl or heterocyclylalkyl having 2 to 9 carbon atoms and 1 to 3 identical or different hereto atoms—in particular nitrogen, oxygen and/or sulphur—each of these phenyl or heterocyclyl radicals optionally being monosubstituted to trisubstituted by identical or different substituents, suitable phenyl or heterocyclyl substituents in each case being those mentioned in the case of $R^1$, $R^6$, $R^7$ independent from each other represents hydrogen, in each case straight-chain or branched alkyl having 1 to 4 carbon atoms, cyanoalkyl having 2 to 3 carbon atoms, alkenyl having 2 to 4 carbon atoms, alkinyl having 2 to 4 carbon atoms, orcycloalkyl, cycloalkylalkyl, cycloalkenyl or cycloalkenylalkyl, each of which has 3 to 6 carbon atoms in the cycloalkyl or cycloalkenyl moiety and, where appropriate, 1 to 3 carbon atoms in the straight-chain or branched alkyl moiety, and each of which is optionally monosubstituted to trisubstituted in the cycloalkyl or cycloalkenyl moiety by identical or different substituents, suitable cycloalkyl or cycloalkenyl substituents in each case being:

halogen, hydroxyl, in each case straight-chain or branched alkyl, alkanediyl, alkoxy, alkoxyalkyl, alkylthio or dialkylamino, each of which has to 3 carbon atoms in the individual alkyl moieties, or in each case straight-chain or branched halogenoalkyl, halogenoalkoxy, halogenoalkylthio, each of which has 1 or 2 carbon atoms and 1 to 5 identical or different halogen atoms, moreover represents phenylalkyl, phenyl, heterocyclylalkyl or heterocyclyl, each of which has, where appropriate, 2 to 9 carbon atoms and 1 to 3 identical or different hetero atoms—in particular-nitrogen, oxygen and/or sulphur—in the heterocyclyl moiety and, where appropriate, 1 to 3 carbon atoms in the straight-chain or branched alkyl moiety, and each of which is optionally monosubstituted to trisubstituted in the phenyl or heterocyclyl moiety by identical or different substituents, suitable aryl or heterocyclyl substituents in each case being those mentioned in the case of $R^1$, or together form a cycloaklylring with 3 to 5 carbon atoms $X^1$ represents oxygen or sulphur, $X^2$ represents oxygen or sulphur and $X^3$ represents oxygen or sulphur, n represents 1 or 2, but where at least one of the substituents $X^1$, $X^2$ and/or $X^3$ represents sulphur.

Reference must be made to the compounds mentioned individually in the preparation examples.

If, for example, $N^\alpha$-(i-propylthio-carbonyl)-L-valine and α-(4-methylphenyl)-ethylamine are used as starting substances, the course of the reaction of the process according to the invention can be represented by the following equation:

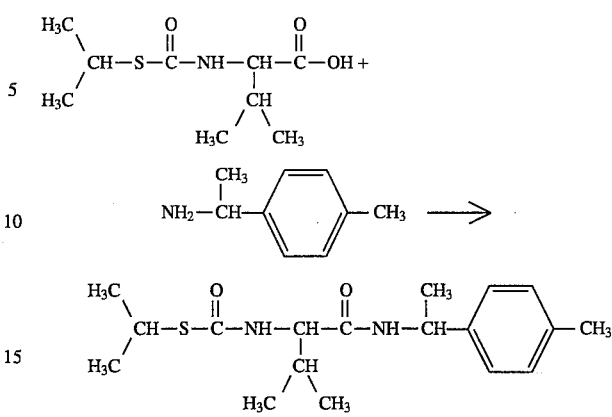

Formula (II) provides a general definition of the substituted amino acids required as starting substances for carrying out the process according to the invention. In this formula (II), $R^1$, $R^2$, $R^3$, $R^4$, $X^1$, $X^2$ and $X^3$ preferably represent those radicals which have already been mentioned in connection with the description of the substances of the formula (I) according to the invention as being preferred for these substituents. The substituted amino acids of the formula (II) are known or can be prepared analogously to known processes (cf., for example, Houben-Weyl "Methoden der organischen Chemie" [Methods in Organic Chemistry] Volume 15/1, 4th Edition, Thieme Verlag Stuttgart 1977; JP 53148530; JP 52151146; J. Org. Chem. 43, 2930–2932 [1978]; J. Chem. Soc., Perkin Trans. 1, 1972, 1983–1985; Chem. Ber. 104, 3156–3167 [1971]; J. Org. Chem. 36, 49–59 [1971]; Helv. Chim. Acta 52, 282–291 [1969]; Tetrahedron 34, 2763–2766 [1978]; Chem. Pharm. Bull. 19, 912–929 [1971]; J. Chem. Soc. 1952, 2076–2079).

Formula (III) provides a general definition of the amines required as starting substances for carrying out the process according to the invention. In this formula (III), $R^5$ and $R^6$ preferably represent those radicals which have already been mentioned in connection with the description of the substances of the formula (I) according to the invention as being preferred for these substituents.

The amines of the formula (III) are generally known compounds of organic chemistry or can be obtained analogously to generally known processes.

Suitable diluents for carrying out the process according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran or ethylene glycol dimethyl ether or ethylene glycol diethyl ether; ketones such as acetone or butanone or methyl isobutyl ketone; nitriles .such as acetonitrile, propionitrile or benzonitrile; amides such as N,N-dimethylformamide, N,N-dimethylacetamide, N-methylformanilide, N-methylpyrrolidone or hexamethylphosphoric triamide, esters such as methyl acetate or ethyl acetate, or sulphoxides such as dimethyl sulphoxide.

If appropriate, the process according to the invention is carried out in the presence of a suitable condensing agent. Suitable condensing agents are all those which can customarily be used for such amidation reactions. Examples which may be mentioned are acid halide formers such as phosphorus tribromide, phosphorus pentachloride, phosphorus oxychloride or thionyl chloride, anhydride formers such as ethyl chloroformate, isobutyl chloroformate or methanesulphonyl chloride, carbodiimides such as N,N'-dicyclohexylcarbodiimide (DCC) or other customary condensing agents such as N,N'-carbonyldiimidazole, 2-ethoxy-N-ethoxycarbonyl-1,2-dihydroquinoline (EEDQ) or triphenylphosphine/carbon tetrachloride.

The process according to the invention is preferably carried out in the presence of a suitable reaction auxiliary. Suitable reaction auxiliaries are all inorganic and organic bases which can customarily be used. The hydrides, hydroxide, amides, alcoholates, carbonates or hydrogen carbonates of alkali metals are preferably used such as, for example, sodium hydride, sodium amide, sodium hydroxide, sodium methylate, sodium ethylate, potassium t-butylate, sodium carbonate or sodium hydrogen carbonate, or else tertiary amines such as, for example, triethylamine, N-methylpiperidine, N,N-dimethylaniline, pyridine, N,N-dimethylaminopyridine, diazabicyclooctane (DABCO), diazabicyclononene (DBN) or diazabicycloundecene (DBU).

When carrying out the process according to the invention, the reaction temperatures can be varied within a substantial range. In general, the process is carried out at temperatures between −60° C. and 220° C., preferably at temperatures between −20° C. and 100° C.

To carry out the process according to the invention, 1.0 to 10.0 moles, preferably 1.0 to 2.0 moles, of amine of the formula (III) and, if appropriate—1.0 to 3.0 moles, preferably 1.0 to 2.0 moles, of condensing agent or reaction auxiliary are generally employed per mole of substituted amino acid of the formula (II). The reaction is carried out and the reaction products are worked up and isolated by generally customary methods (cf., in this context, for example Houben Weyl "Methoden der organischen Chemie" [Methods in Organic Chemistry], Volume 15/2, 4th Edition, Thieme Verlag Stuttgart 1977 or the Preparation Examples). The end products of the formula (I) are purified with the aid of customary processes, for example by column chromatography or by recrystallisation.

They are characterised with the aid of the melting point or, in the case of non-crystallising compounds, with the aid of proton nuclear resonance spectroscopy ($^1$H NMR).

The active compounds according to the invention have a powerful action against pests and can be employed in practice for combating undesired harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Pythium species, such as, for example, *Pythium ultimum*;
Phytophthora species, such as, for example, *Phytophthora infestans*;
Pseudoperonospora species, such as, for example, *Pseudoperonospora humuli* or *Pseudoperonospora cubensis*;
Plasmopara species, such as, for example, *Plasmopara viticola*;
Peronospora species, such as, for example, *Peronospora pisi* or *P. brassicae*;
Erysiphe species, such as, for example, *Erysiphe graminis*;
Sphaerotheca species, such as, for example, *Sphaerotheca fuliginea*;
Podosphaera species, such as, for example, *Podosphaera leucotricha*;
Venturia species, such as, for example, *Venturia inaequalis*;
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus*;
Puccinia species, such as, for example, *Puccinia recondita*;
Tilletia species, such as, for example, Tilletia caries; Ustilago species, such as, for example, *Ustilago nuda* or *Ustilago avenae*;
Pellicularia species, such as, for example, *Pellicularia sasakii*;
Pyricularia species, such as, for example, *Pyricularia oryzae*;
Fusarium species, such as, for example, *Fusarium culmorum*;
Botrytis species, such as, for example, *Botrytis cinerea*;
Septoria species, such as, for example, *Septoria nodorum*;
Leptosphaeria species, such as, for example, *Leptosphaeria nodorum*;
Cercospora species, such as, for example, *Cercospora canescens*;
Alternaria species, such as, for example, *Alternaria brassicae* and
Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success for combating diseases .in fruit and vegetable growing such as, for example, against the causative of tomato rot (Phytophthora inf estans).

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methylethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present is the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%. In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

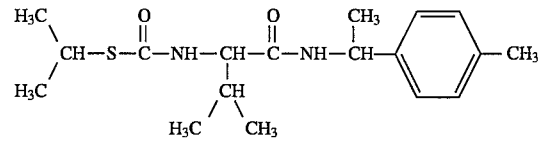

To 3.28 g (0.015 mol) of $N^\alpha$-(i-propylthio-carbonyl)-L-valine in 50 ml of dichloromethane there are added, at −20° C. 1.5 g (0 015 mol) of N-methylpiperidine and subsequently dropwise and with stirring at −20° C. 2.0 g (0.015 mol) of isobutyl chloroformate and, after the addition has ended, the mixture is stirred for a further 10 minutes at −20° C. and then cooled to −60° C. and 2.0 g (0.015 mol) of α-(4-methylphenyl)-ethylamine are added, during which process the temperature should not rise above −15° C. The mixture is subsequently stirred for a further 2 hours at. −15° C. and 15 hours at room temperature, solid which has precipitated is then filtered off and washed with dichloromethane, the filtrate is concentrated in vacuo, the residue is taken up in water, the mixture is extracted several times using ethyl acetate, and the combined ethyl acetate phases are washed with aqueous sodium hydrogen carbonate solution and water and dried over sodium sulphate, and the solvent is removed in vacuo.

2.8 g (58% of theory) of $N^\alpha$- (i-propylthio-carbonyl)-L-valine-[ N-(4-methylphenyl)-ethylamide] of melting point 168° C. are obtained.

Preparation of the starting compound:

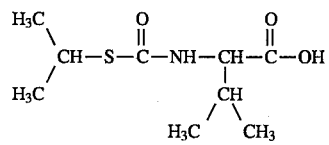

To 37.5 g (0.32 mol) of L-valine and 88.0 g (0.64 mol) of potassium carbonate in 400 ml of water there are added dropwise with stirring and ice-cooling 45 g (0.32 mol) of isopropyl chlorothioformate and, when the addition has ended, the mixture is stirred for a further hour at 0° C., acidified with concentrated hydrochloric acid and extracted three times using 200 ml portions of toluene, and the combined organic phases are dried over sodium sulphate, and the solvent is removed in vacuo. The viscous oil which remains crystallises after some time. 37.2 g (53% of theory) of $N^\alpha$-(i-propylthio-carbonyl)-L-valine of melting point 65° C. are obtained.

The following substituted amino acid amides of the general formula (I) are obtained analogously and following the general preparation instructions:

$$R^1-X^1-\underset{\underset{X^2}{\|}}{C}-\underset{\underset{R^4}{|}}{\overset{\overset{R^2}{|}}{N}}-\underset{\underset{R^4}{|}}{\overset{\overset{R^3}{|}}{C}}-\overset{\overset{X^3}{\|}}{C}-NH-CH\underset{R^6}{\overset{R^5}{\diagdown}} \quad (I)$$

| Ex. No. | $R^1$ | $R^2$ | $R^3$ | $R^4$ | $R^5$ | $R^6$ | $X^1$ | $X^2$ | $X^3$ | m.p./°C.*) |
|---|---|---|---|---|---|---|---|---|---|---|
| 2 | i-$C_3H_7$ | H | H | i-$C_3H_7$ | $CH_3$ | ![4-Cl-C6H4] | S | O | O | 189 (rac.) |
| 3 | i-$C_3H_7$ | H | H | i-$C_3H_7$ | $CH_3$ | ![4-OCH3-C6H4] | S | O | O | 170 (rac.) |
| 4 | i-$C_3H_7$ | H | H | i-$C_3H_7$ | $CH_3$ | ![4-C2H5-C6H4] | S | O | O | 148 (rac.) |
| 5 | i-$C_3H_7$ | H | H | i-$C_3H_7$ | $CH_3$ | $C_6H_5$ | S | O | O | 179 |
| 6 | i-$C_3H_7$ | H | H | i-$C_3H_7$ | $CH_3$ | ![4-Cl-C6H4] | S | O | O | 191 (R+) |
| 7 | i-$C_3H_7$ | H | H | i-$C_3H_7$ | $CH_3$ | $C_6H_5$ | S | O | O | 199 (R+) |
| 8 | i-$C_3H_7$ | H | H | i-$C_3H_7$ | $CH_3$ | $C_6H_5$ | S | O | O | 176 (rac.) |
| 9 | i-$C_3H_7$ | H | H | i-$C_3H_7$ | $CH_3$ | ![4-OC2H5-C6H4] | S | O | O | 196 (rac.) |
| 10 | i-$C_3H_7$ | H | H | i-$C_3H_7$ | $CH_3$ | ![4-F-C6H4] | S | O | O | 204 (rac.) |
| 11 | t-$C_4H_9$ | H | H | i-$C_3H_7$ | $CH_3$ | ![4-CH3-C6H4] | S | O | O | 179 (rac.) |

*)The stereochemical data in each case relate to the amine component in the amide moiety. Exclusively L-amino acid derivatives were employed as starting compounds of the formula (II).

Use Example

In the use example which follows, the compound listed below were employed as comparison substance:

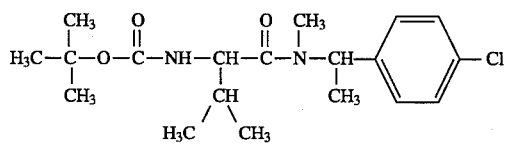

(A)

$N^\alpha$-(t-butyloxycarbonyl)-L-valine-{N-methyl-N-[14-chlorophenyl)-ethyl]-amide}-(1-

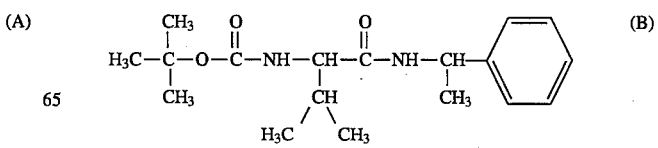

(B)

N$^\alpha$-(t-butyloxcarbonyl)-L-valine-[N-(1-phenylethyl)-amide]

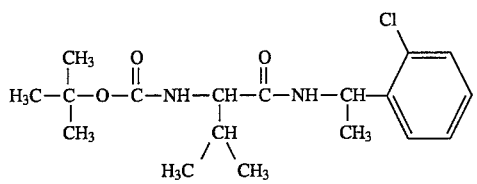
(C)

N$^\alpha$-(t-butyloxycarbonyl)-L-valine-{N-[1-(2-chlorophenyl)ethyl]-amide}
(disclosed in EP 398,072)

Example A

Phytophthora test (tomato)/protective

Solvent: 4.7 parts by weight of acetone

Emulsifier: 0.3 parts by weight of alkyl-aryl polyglycol ether

To produce a suitable preparation of active compound, one part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are then placed in an incubation cabinet at 20° C. under relative atmospheric humidity of approx. 100%.

The evaluation is effected 3 days after inoculation.

In this test, a clearly superior activity compared with the prior art is shown, for example, by the compounds of the Preparation Example 1, 2, 3, 4, 5, 7, 10 and 11 and which show a degree of activity of up to 100% at an active compound concentration of 100 ppm.

We claim:

1. An amino acid amine of the formula

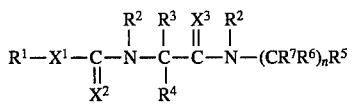

in which
R$^1$ represents alkyl having 2 to 5 carbon atoms,
R$^2$ represents hydrogen, alkyl or cycloalkyl,
R$^3$ represents alkyl having 1 to 6 carbon atoms,
R$^4$ represents hydrogen,
R$^5$ represents phenyl optionally substituted by at least one member selected from the group consisting of fluorine, chlorine, or alkyl or alkoxy having 1 to 3 carbon atoms,
R$^6$ represents hydrogen,
R$^7$ represents alkyl having 1 to 4 carbon atoms,
X$^1$ represents sulphur,
X$^2$ represents oxygen,
X$^3$ represents oxygen, and
n represents 1, 2 or 3.

2. A compound according to claim 1, in which n represents 1.

3. A compound according to claim 2, in which
R$^1$ represents isopropyl,
R$^3$ represents isopropyl,
R$^5$ represents phenyl optionally substituted by at least one member selected from the group consisting of fluorine, chlorine, Methyl, ethyl or methoxy, and
R$^7$ represents methyl.

4. A fungicidal composition comprising a fungicidally effective amount of a compound according to claim 1 and a diluent.

5. A method of combatting fungi which comprises applying to such fungi or to a fungus habitat a fungicidally effective amount of a compound according to claim 1.

6. A compound selected from the group consisting of:

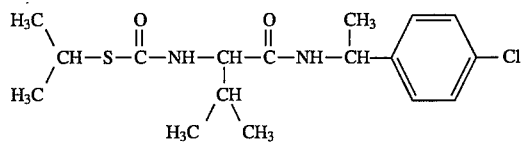

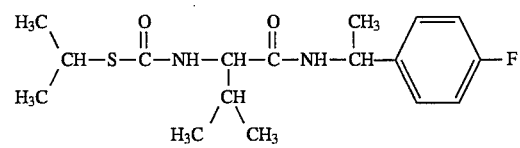

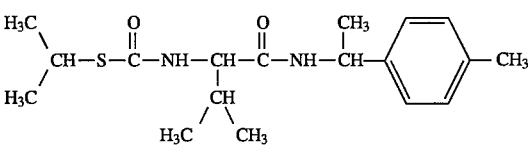

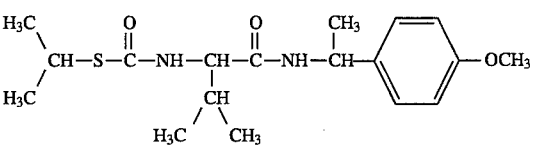

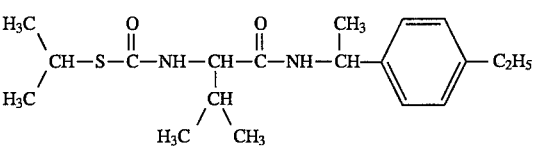

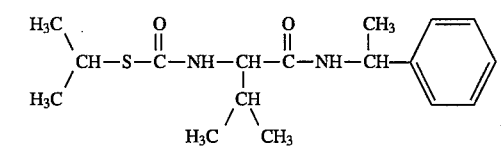

7. The compound according to claim 6, wherein such compound is N$^\alpha$-(i-propylthio-carbonyl)-L-valine-[N-(4-methylphenyl)ethylamide] of the formula

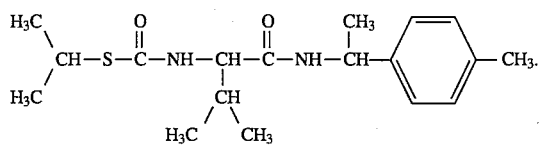

8. A compound according to claim 6, wherein such compound is

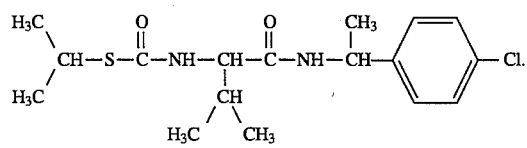

9. A compound according to claim 6, wherein such compound is

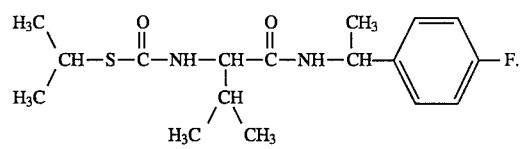

10. A compound according to claim 6, wherein such compound is

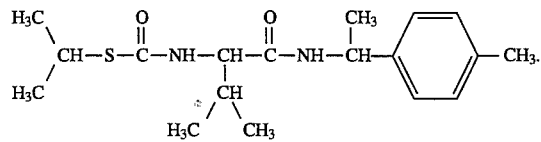

11. A compound according to claim 6, wherein such compound is

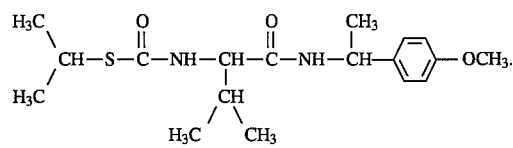

12. A compound according to claim 6, wherein such compound is

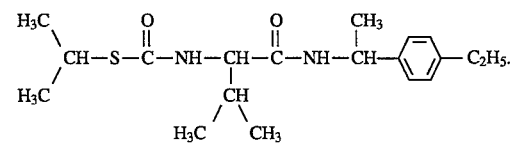

13. A compound according to claim 6, wherein such compound is

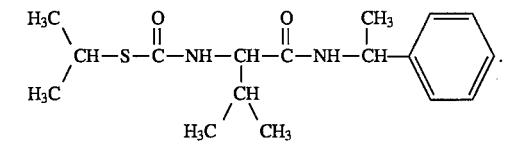

14. A fungicidal composition comprising a fungicidally effective amount of a compound according to claim 6, and a diluent.

15. A method of combatting fungi which comprises applying to such fungi or to a fungus habitat a fungicidally effective amount of a compound according to claim 6.

* * * * *